(12) United States Patent
Armbruster et al.

(10) Patent No.: US 7,851,163 B2
(45) Date of Patent: Dec. 14, 2010

(54) METHOD FOR DETERMINING THE BIOLOGICALLY EFFECTIVE PARATHYROID HORMONE ACTIVITY IN A SAMPLE

(75) Inventors: Franz Paul Armbruster, Bensheim (DE); Albert Missbichler, Vienna (AT); Heinrich Schmidt-Gayk, Neustadt-Hambach (DE); Heinz-Jürgen Roth, Ilvesheim (DE)

(73) Assignee: Immundiagnostik, AG, Bensheim (DE)

( * ) Notice: Subject to any disclaimer, the term of this patent is extended or adjusted under 35 U.S.C. 154(b) by 939 days.

(21) Appl. No.: 10/168,185

(22) PCT Filed: Dec. 18, 2000

(86) PCT No.: PCT/EP00/12911

§ 371 (c)(1), (2), (4) Date: Mar. 21, 2003

(87) PCT Pub. No.: WO01/44818

PCT Pub. Date: Jun. 21, 2001

(65) Prior Publication Data

US 2003/0175802 A1    Sep. 18, 2003

(30) Foreign Application Priority Data

Dec. 17, 1999  (DE)  ................. 199 61 350

(51) Int. Cl.
*G01N 33/53* (2006.01)
(52) U.S. Cl. ........................ 435/7.1; 435/7.2
(58) Field of Classification Search ............... 435/7.1, 435/7.2, 7.92, 7.94, 39, 7.91
See application file for complete search history.

(56) References Cited

U.S. PATENT DOCUMENTS 6,030,790 A    2/2000  Adermann et al.
6,689,566 B1 *  2/2004  Cantor et al. ................ 435/7.1

FOREIGN PATENT DOCUMENTS

WO    WO 96/10041 A1    4/1996

OTHER PUBLICATIONS

Gardella et al. Endocrinology 1993 vol. 132, p. 2024-30.*
Pellegrini et al. Biochemistry 1998 vol. 37, p. 12737-43.*
Barbier et al. Biochemistry 2000 vol. 39, p. 14522-30.*
Blind, E. et al. Measurement of intact human parathyrin by an extracting two-site immunoradiometric assay. *Clinical Chemistry*, 1987;33(8):1376-1381.
Mägerlein, M. et al. A new immunoenzymometric assay for bioactive N-terminal human parathyroid hormone fragments and its application in pharmacokinetic studies in dogs. *Arzneimittelforschung*, Feb. 1998;48(2):199-204.
Re-examination of US-6,030,790, Control No. 90007412.

* cited by examiner

*Primary Examiner*—Jacob Cheu
(74) *Attorney, Agent, or Firm*—Lahive & Cockfield, LLP; Jane E. Remillard, Esq.; Jill Gorny Sloper, Esq.

(57) ABSTRACT

Immunoassay for the determination of parathyroid hormone activity in a sample, and for the diagnosis, etiology and treatment of calcium metabolism disturbances, osteopathies and hyper- or hypoparathyroidisms. The parathyroid hormone activity is measured with the aid of an antibody which binds to an epitope in the region of the receptor binding structure 15 to 22 of the parathyroid hormone, and an antibody which recognizes whether the amino-terminal end 1 to 3 of the parathyroid hormone is intact. The assay permits the antagonistic characteristics of some parathyroid hormone fragments to be taken into account.

4 Claims, 4 Drawing Sheets

Figure 1A:
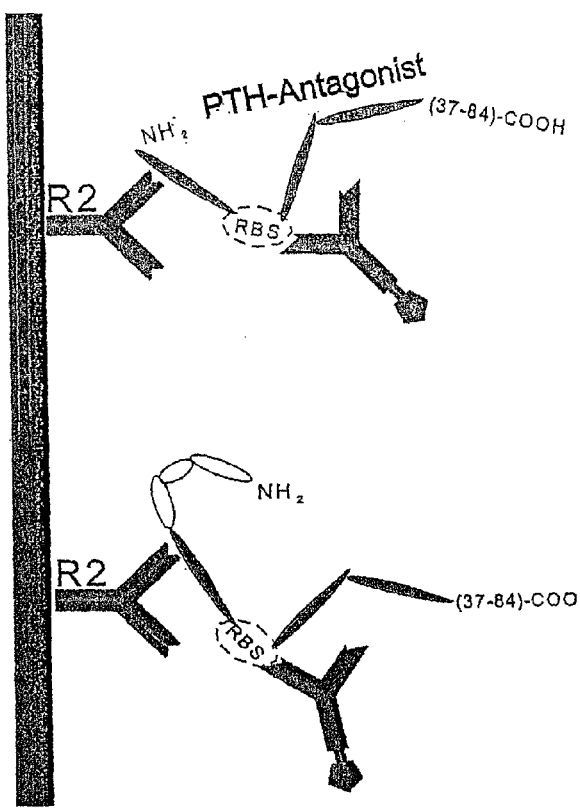

```
                        15       22
            123              RECEPTOR
Human:    SVS  EIQLMHNLGKH  LNSMERVE  WLRKKLQDVHNFVAL
Bovine:   AVS  EIQFMHNLGKH  LSSMERVE  WLRKKLQDVHNFVAL
Rat:      AVS  EIQLMHNLGKH  LASVERMQ  WLRKKLQDVHNFVSL
Porcine:  SVS  EIQLMHNLGKH  LSSLERVE  WLRKKLQDVHNFVAL
Canine:   SVS  EIQFMHNLGKH  LSSMERVE  WLRKKLQDVHNFVAL
```

Cross-reactivity and Epitopes of mAK

```
                       SEQUENCE LISTING

<160> NUMBER OF SEQ ID NOS: 16

<210> SEQ ID NO 1
<211> LENGTH: 10
<212> TYPE: PRT
<213> ORGANISM: Homo sapiens

<400> SEQUENCE: 1

Ser Val Ser Glu Ile Gln Leu Met His Asn
1               5                   10

<210> SEQ ID NO 2
<211> LENGTH: 9
<212> TYPE: PRT
<213> ORGANISM: Homo sapiens

<400> SEQUENCE: 2

Ser Val Ser Glu Ile Gln Leu Met His
1               5

<210> SEQ ID NO 3
<211> LENGTH: 8
<212> TYPE: PRT
<213> ORGANISM: Homo sapiens

<400> SEQUENCE: 3

Ser Val Ser Glu Ile Gln Leu Met
1               5

<210> SEQ ID NO 4
<211> LENGTH: 7
<212> TYPE: PRT
```

```
<213> ORGANISM: Homo sapiens

<400> SEQUENCE: 4

Ser Val Ser Glu Ile Gln Leu
1               5

<210> SEQ ID NO 5
<211> LENGTH: 6
<212> TYPE: PRT
<213> ORGANISM: Homo sapiens

<400> SEQUENCE: 5

Ser Val Ser Glu Ile Gln
1               5

<210> SEQ ID NO 6
<211> LENGTH: 5
<212> TYPE: PRT
<213> ORGANISM: Homo sapiens

<400> SEQUENCE: 6

Ser Val Ser Glu Ile
1               5

<210> SEQ ID NO 7
<211> LENGTH: 9
<212> TYPE: PRT
<213> ORGANISM: Homo sapiens

<400> SEQUENCE: 7

Val Ser Glu Ile Gln Leu Met His Asn
1               5

<210> SEQ ID NO 8
<211> LENGTH: 8
<212> TYPE: PRT
<213> ORGANISM: Homo sapiens

<400> SEQUENCE: 8

Ser Glu Ile Gln Leu Met His Asn
1               5

<210> SEQ ID NO 9
<211> LENGTH: 37
<212> TYPE: PRT
<213> ORGANISM: Homo sapiens

<400> SEQUENCE: 9

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu
        35

<210> SEQ ID NO 10
<211> LENGTH: 8
<212> TYPE: PRT
<213> ORGANISM: Homo sapiens

<400> SEQUENCE: 10

Leu Asn Ser Met Glu Arg Val Glu
1               5
```

```
<210> SEQ ID NO 11
<211> LENGTH: 10
<212> TYPE: PRT
<213> ORGANISM: Homo sapiens

<400> SEQUENCE: 11

Ser Val Ser Glu Ile Gln Lys Lys Lys Ala
1               5                   10

<210> SEQ ID NO 12
<211> LENGTH: 37
<212> TYPE: PRT
<213> ORGANISM: Bos sp.

<400> SEQUENCE: 12

Ala Val Ser Glu Ile Gln Phe Met His Asn Leu Gly Lys His Leu Ser
1               5                   10                  15

Ser Met Glu Arg Val Glu Trp Leu Arg Lys Lys Leu Gln Asp Val His
            20                  25                  30

Asn Phe Val Ala Leu
        35

<210> SEQ ID NO 13
<211> LENGTH: 37
<212> TYPE: PRT
<213> ORGANISM: Rattus sp.

<400> SEQUENCE: 13

Ala Val Ser Glu Ile Gln Leu Met His Asn Leu Gly Lys His Leu Ala
1               5                   10                  15

Ser Val Glu Arg Met Gln Trp Leu Arg Lys Lys Leu Gln Asp Val His
            20                  25                  30

Asn Phe Val Ser Leu
        35

<210> SEQ ID NO 14
<211> LENGTH: 37
<212> TYPE: PRT
<213> ORGANISM: Sus sp.

<400> SEQUENCE: 14

Ser Val Ser Glu Ile Gln Leu Met His Asn Leu Gly Lys His Leu Ser
1               5                   10                  15

Ser Leu Glu Arg Val Glu Trp Leu Arg Lys Lys Leu Gln Asp Val His
            20                  25                  30

Asn Phe Val Ala Leu
        35

<210> SEQ ID NO 15
<211> LENGTH: 37
<212> TYPE: PRT
<213> ORGANISM: Canis sp.

<400> SEQUENCE: 15

Ser Val Ser Glu Ile Gln Phe Met His Asn Leu Gly Lys His Leu Ser
1               5                   10                  15

Ser Met Glu Arg Val Glu Trp Leu Arg Lys Lys Leu Gln Asp Val His
            20                  25                  30

Asn Phe Val Ala Leu
        35
```

```
<210> SEQ ID NO 16
<211> LENGTH: 84
<212> TYPE: PRT
<213> ORGANISM: Homo sapiens

<400> SEQUENCE: 16

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser His Glu
        50                  55                  60

Lys Ser Leu Gly Glu Ala Asp Lys Ala Asp Val Asn Val Leu Thr Lys
65                  70                  75                  80

Ala Lys Ser Gln
```

METHOD FOR DETERMINING THE BIOLOGICALLY EFFECTIVE PARATHYROID HORMONE ACTIVITY IN A SAMPLE

This application claims the benefit of prior-filed German patent application DE 199 61 350.8 (filed Dec. 17, 1999) entitled "Method For Determining The Biologically Effective Parathyroid Hormone Activity In a Sample". The entire content of the above-referenced application is incorporated herein by reference.

The invention relates to a method for determining the parathyroid hormone activity in a sample. The invention relates in particular to the immunological determination of the activity of parathyroid hormone (PTH) and its fragments in a body fluid, for diagnosis, etiology and treatment of disturbances of the calcium metabolism, osteopathies and hyper- or hypeparathyroidisms.

Human parathyroid hormone (see SWISS-PROT: P01270 (SEO ID NO: 16), PTHY-HUMAN) is a linear peptide of 84 amino acids (MW 9500 Da) of the parathyroid (Glandulae parathyroideae). It increases the calcium content and reduces the phosphate content of the blood and takes part in the mobilisation of the extracellular hydroxyapatite of the bones. The PTH content of the blood is thus an important diagnostic parameter with patients having disturbed calcium metabolism and knowledge thereof is necessary for determining 1) presence and degree of hyper- or hypo-parathyroidism, 2) quantification of osteoblast activity, 3) quantification of osteoclast activity, 4) monitoring of treatment with vitamin D and active vitamin D metabolites, 5) estimation of presence of aluminium, 6) estimation of a possible oestrogen deficiency in post-menopausal dialysis patients, 6) the required steroid or cyclosporin dose after kidney transplantation, 7) the need for treatment or prevention of bone marrow changes, uraemic conditions and chronic kidney failure.

The determination of the effective PTH activity in the blood is problematic, since the peptide hormone is rapidly decomposed into active and inactive fragments in the circulation and by the liver, for example through cleaving in the region of amino acids 34 to 37. Further, the physiological concentration of intact human PTH (hPTH) in blood plasma is only about 1 to 5 pMol/L.

In the state of the art, the determination of intact hPTH (1-84) is effected by means of the immunological detection of two mutually widely separated epitopes on the peptide. However, despite this there are many patients with 8 to 10 times increased content of intact PTH (1-84) in the blood and low-normal bone specific alkaline phosphatase (ostase), which means free from symptoms of excessive PTH activity. This has been explained away as false measurements or a PTH resistance of the osteoblasts, for example due to a genetically reduced expression of PTH receptors. The determination of the effective PTH activity is further complicated in that some PTH fragments have an activity comparable with intact hPTH (1-84) (see EP-A 0 349 545), whereas other PTH fragments have an antagonistic effect (see LePage et al (1998), Clinical Chemistry, 44:4, pp 805-809; Schmidt-Gayk et al. (1999) Osteologie forum, 5, pp 48-58, and the references there given. Thus, one knows that the fragments hPTH (3-34) and hPTH (7-34) inhibit the effects of the PTH (Suva et al. (1987) Science, 237, 893ff; EP 0 451 867).

WO 96/10041 teaches that antibodies against amino-terminal epitopes of PTH recognise biologically active PTH and that in the case of a loss of the amino-terminal amino acids serine and valine the activity is lost.

Maegerlein et al. describe in Arzneim.-Forsch./Drug Res. 48(I), pp 197-204 (1998) an immunoenzymometric assay for the determination of the concentration of injected PTH fragment 1-37 in pharmacokinetic studies on dogs. The measurement range of the assay extends from 100 to 4 pMol/L and ends above the physiological PTH levels normally present in serum.

The true biologically effective PTH activity in a sample can at the present time be determined, if at all, only through the effect on a cellular system such as for example pheochromocyte cells (PC-12).

It is the object of the invention to provide a method for determining the overall effective parathyroid hormone activity in a sample.

This object is achieved by means of a method according to claim 1. Further advantageous embodiments of the method are indicated in the dependent claims. The invention also relates to a test system and method for the diagnosis and assessment of the degree of an hypo- or hyper-parathyroidism, and the determination of causes of disturbances of the calcium metabolism, osteopathies, kidney failure and diseases, which arise from a disturbed homeostasis of the calcium and phosphate content of the blood.

The method in accordance with the invention, for determining the biological effective PTH activity in a sample, is characterised by the steps: (i) reacting the sample with an antibody which binds to an epitope on the PTH, which is located in the vicinity of the binding structure on the PTH receptor; (ii) reacting the sample with an antibody which recognises an epitope which is formed of the terminal amino acids 1 to 3 of the PTH; (iii) determination of the quantity of molecules which are recognised by the two antibodies; and (iv) calculation of the biologically effective PTH activity in the sample.

The above-mentioned antibodies preferably recognise epitopes of human PTH. The antibody against the receptor binding structure binds preferably an epitope in which at least one of the amino acids 15 to 22 of human PTH is involved. The invention further includes a method in which a first antibody is bound to a solid phase. The second antibody may carry a marker or be conjugated with an enzyme such as alkaline phosphatase or peroxidase. The method is effected in accordance with the invention in a per se known immunoassay, preferably in an ELISA, IEMA, ILMA or LIA. The binding of the two antibodies to the PTH is effected preferably in the presence of 0.05 to 0.1 weight percent of a mild detergent such as Tween™-20 or Triton™-X-100, so that a folding of the amino-terminal epitope PTH (1-3) to the PTH receptor binding structure is prevented, or to maintain the amino-terminal epitope PTH (1-3) accessible for the binding of the antibody. Since for the biological activity of PTH both the receptor binding structure and also the amino-terminal epitope PTH (1-3) are necessary, these two structures may probably interact with one another. Through the presence of a mild detergent, the sensitivity and accuracy of the assay can be significantly increased.

In one exemplary embodiment of the method a known aliquot of the sample is further reacted with antibodies which bind to the PTH sequences between amino acids 4 to 14 and 15 to 37. The number of molecules in a sample which bind antibodies against the epitope PTH (1-3) and the receptor binding structure of the PTH, and the number of molecules which bind antibodies against the PTH regions 4 to 14 and 15 to 37, are then brought into relationship one with another and the biologically effective PTH activity determined.

The invention further relates to a diagnostic system for determining the PTH activity in a sample which is characterised by antibodies which specifically recognise the PTH epitope having the amino acids 1 to 3 and antibodies which bind to the region of the PTH receptor binding structure. In one embodiment, the diagnosis further has antibodies which bind specifically to the region between amino acids 4 and 14. In further embodiments the system contains antibodies which bind to the section between amino acids 24 and 37 of the parathyroid hormone or to the mid-regional range (53 to 68) or to the C-terminal (53 to 84) range of the peptide hormone.

In contrast to earlier immunoassays, the method in accordance with the invention takes into account the PTH activity of the non-intact PTH fragments and that apparently intact PTH is biologically inactive if the last or the last two amino-terminal amino acids of the peptide hormone are missing. Also the antagonistic activity of some PTH fragments is taken into account in the determination, in that with the method not only the agonistic but also the antagonistic PTH fragments can be determined. The antagonistic activity is derived from the excess of PTH receptor binding structure to intact PTH amino-terminals, i.e. from the number of PTH fragments which, although they contain the binding structure for the PTH receptor, have no intact amino-terminal end. PTH fragments which have neither a receptor binding structure with the amino acids 15 to 22 nor an intact amino-terminal epitope PTH (1-3) have no agonistic or antagonistic activity.

Conventional immunological assays for so-called "truly intact" hPTH (1-84) or hPTH (1-37) yield falsely high activity values, since physiological activity is deduced from the presence of functionally insignificant epitopes. They do not take into account that the correct folding or the binding to the PTH receptor is dependent upon an intact amino-terminus having the amino acids $H_2N$-$Ser^1$-$Val^2$. The PTH fragments often determined as "active" in conventional assays—hPTH (7-84), hPTH(3-84) or hPTH(4-37)—have, however, either no or antagonistic activity. Assays on the basis of antibodies against the mid-regional (53-68) or C-terminal (53-84) section in contrast overlook biologically active PTH fragments of the types hPTH(1-37), hPTH(1-32~36) or hPTH(1-38).

With immunoassays on the basis of antibodies against the amino-terminal region of PTH, or against peptides of the hPTH(1-37) sequence, false activities are also determined, since on the one hand the antagonistic activity of various fragments is not detected and on the other hand no positive determination of the biologically active structural unit is effected. With polyclonal antibodies or antisera against the amino-terminal peptide having the amino acids 1 to 5 or 6, in part even antagonistically effective PTH fragments are recognised as active PTH fragments.

The method in accordance with the invention thus makes available to the doctor PTH activity values which indicate the physiological effect of the PTH fragments. Thus, there are patients having hyperparathyroidism, who have normal or reduced amounts of intact hPTH(1-84) in the serum. The hyperparathyroidism can then arise in that these patients secrete into the bloodstream the likewise active PTH fragments hPTH(1-37) and hPTH(1-38), so that they suffer from an excessive PTH activity and the consequences thereof.

Figure 1B:
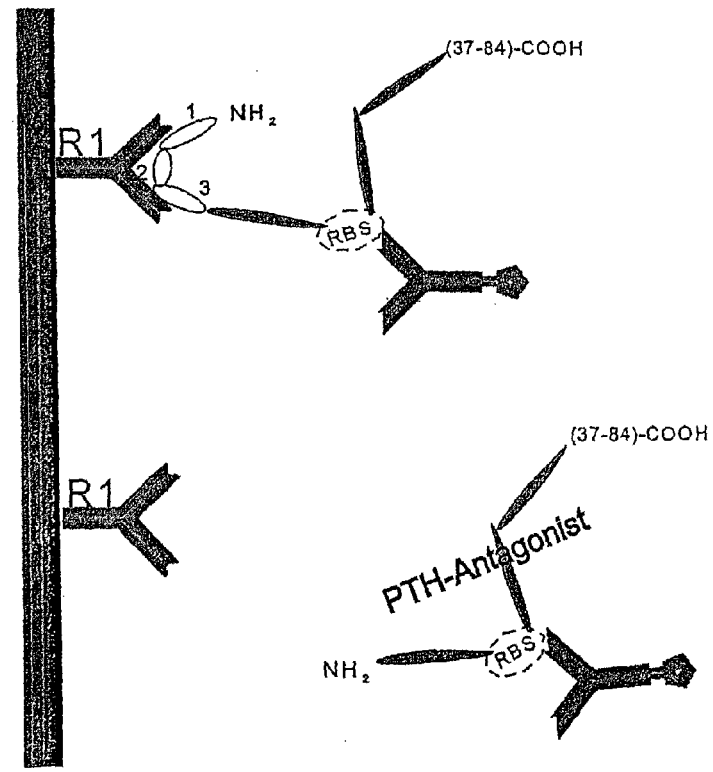
Figures 2, 3:
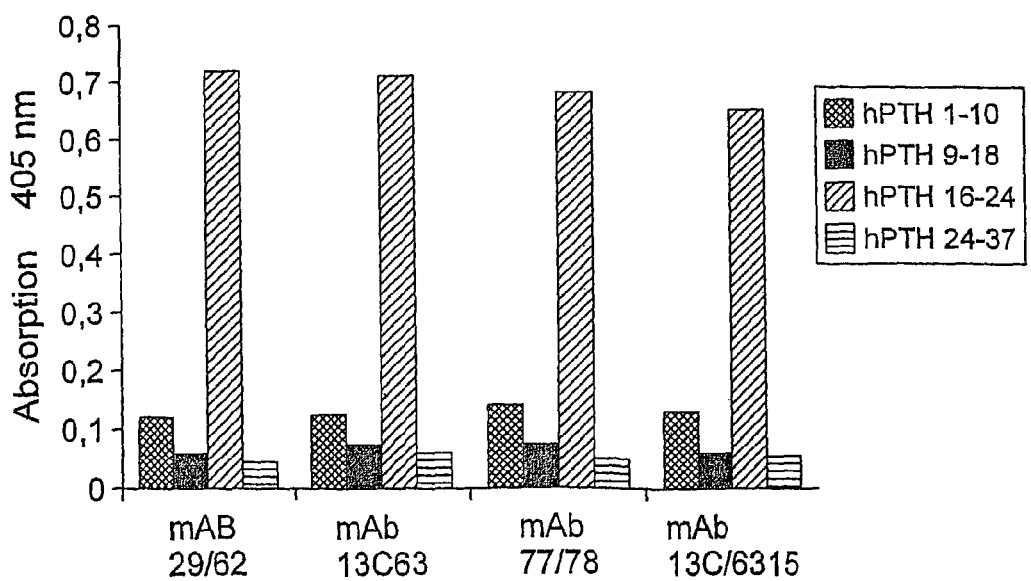
Figure 4A:
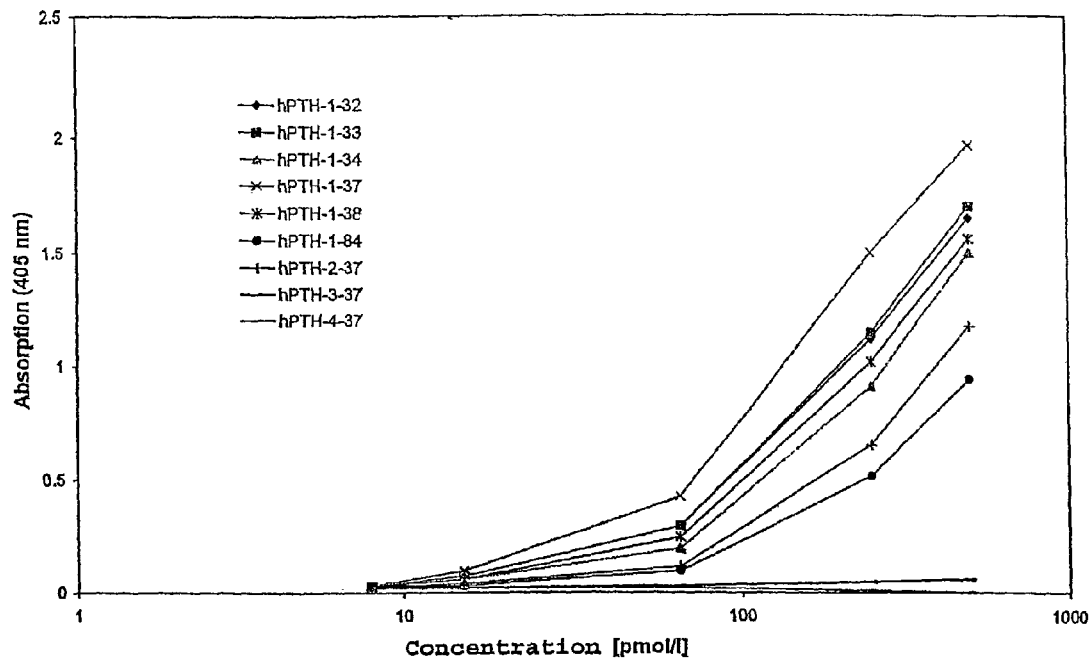
Figure 4B:
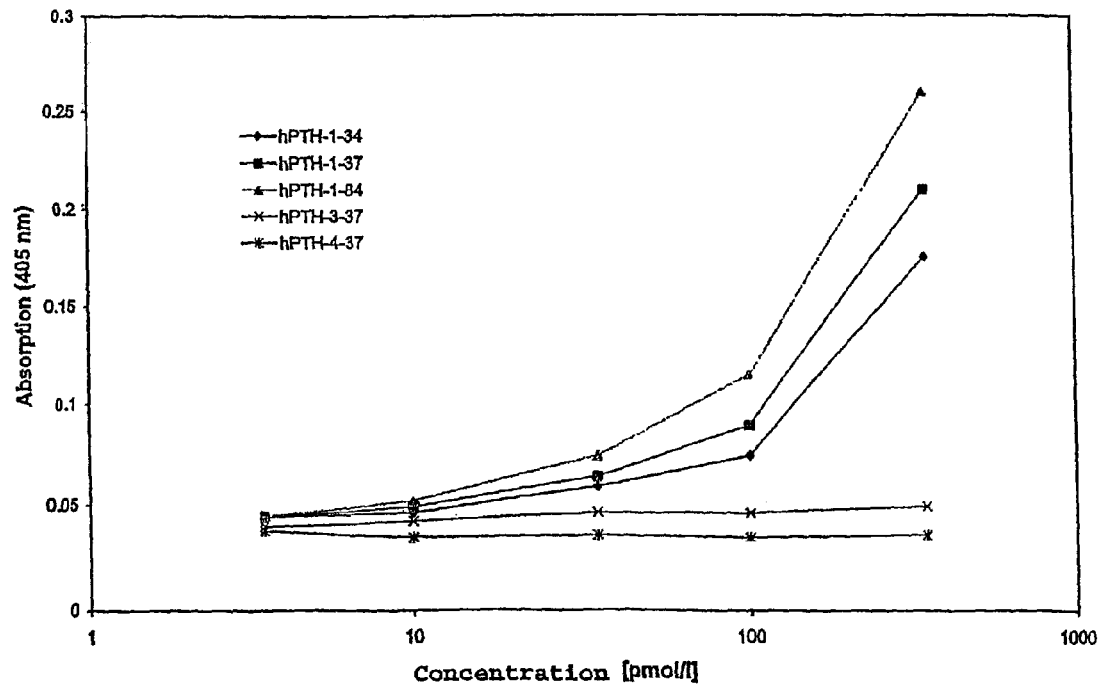
Figure 5:
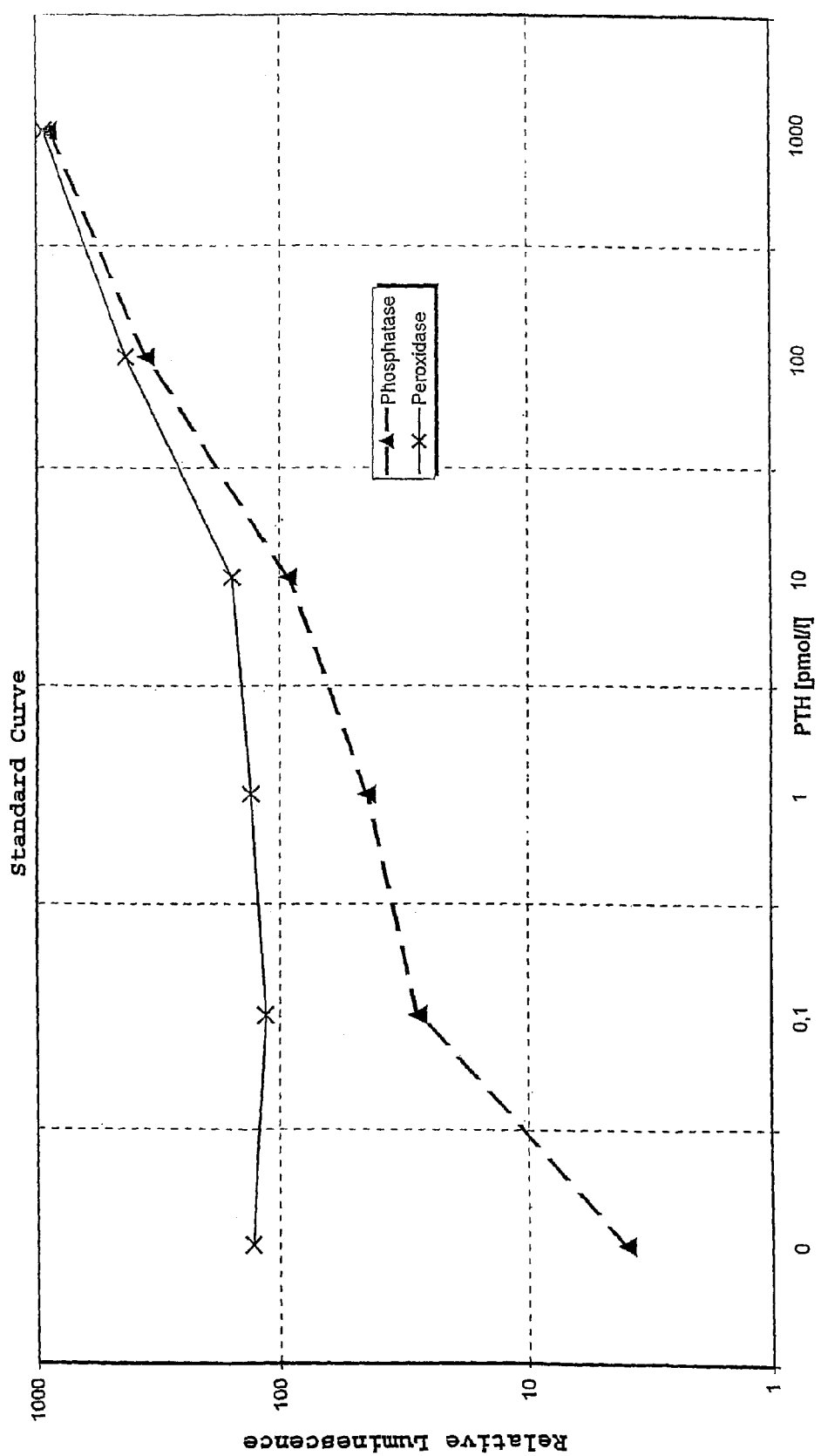

Further advantages, features and embodiments of the invention will be understood from the following examples and the accompanying drawings, which show:

FIG. 1 an outline representation of the method in accordance with the invention;

FIG. 2 a comparison of the amino-terminal PTH sequences and of the receptor binding structure of humans (SEQ ID NO: 9), cattle (SEQ ID NO: 12), rats (SEQ ID NO: 13), pigs (SEQ ID NO: 14) and dogs (SEQ ID NO: 15);

FIG. 3 an analysis of the binding epitopes of monoclonal antibodies against the receptor binding point of PTH and their cross-reactions with neighbouring PTH fragments;

FIG. 4a,b an analysis of the cross-reaction with various hPTH fragments in an immunoenzymometric assay;

FIG. 5 a standard curve of the LIA assay in accordance with the invention for the determination of the effective PTH activity in a sample.

See FIG. 1 with the outline of the method according to the invention. The antibodies against the amino-terminal epitope of the human PTH having the amino acids $H_2N$-$Ser^1$-$Val^2$-$Ser^3$ are obtained in that one brings about an immune reaction against one of the following peptides.

SEQ No. 1:
$H_2N$-$Ser^1$-$Val^2$-$Ser^3$-$Glu^4$-$Ile^5$-$Gln^6$-$Leu^7$-$Met^8$-$His^9$-$Asn^{10}$-OH

SEQ No. 2:
$H_2N$-$Ser^1$-$Val^2$-$Ser^3$-$Glu^4$-$Ile^5$-$Gln^6$-$Leu^7$-$Met^8$-$His^9$-OH

SEQ No. 3:
$H_2N$-$Ser^3$-$Val^2$-$Ser^3$-$Glu^4$-$Ile^5$-$Gln^6$-$Leu^7$-$Met^8$-OH

SEQ No. 4:
$H_2N$-$Ser^1$-$Val^2$-$Ser^3$-$Glu^4$-$Ile^5$-$Gln^6$-$Leu^7$-OH

SEQ No. 5:
$H_2N$-$Ser^1$-$Val^2$-$Ser^3$-$Glu^4$-$Ile^5$-$Gln^6$-OH

SEQ No. 6:
$H_2N$-$Ser^1$-$Val^2$-$Ser^3$-$Glu^4$-$Ile^5$-OH

The synthesis of these peptides is effected in known manner preferably on a lysine framework on a Wang resin. For this purpose, initially there is coupled to a C-terminal amino acid bonded to a Wang resin, in three coupling cycles, in each case Fmoc-L-lysine(Fmoc)-OH. By means of cleaving off of the protecting groups with piperidine there are obtained eight free amino functions, on which the amino-terminal sequence of human parathyroid hormone can be synthesised.

The Wang resin with the amino-terminal PTH amino acid sequence may then be directly injected—preferably together with complete Freund's adjuvant—into an animal, for example into mice, rats, rabbits or goats, for immunisation. The amino-terminal PTH peptide can also be cleaved off before an immunisation, isolated and coupled with a carrier protein such as ovalbumin, cattle albumin, thyreoglobulin or haemocyanin, for example with dicyclohexylcarbodiimide. After several booster immunisations there is isolated the immunoglobulin fraction which has an antibody titre against the amino-terminal PTH peptide.

With the above-mentioned amino-terminal peptides there are regularly obtained antibodies which recognise an epitope of the first two amino-terminal amino acids of hPTH. A fraction having antibodies purely against the amino-terminal epitop hPTH(1-3) can be obtained by means affinity chromatography, whereby a hPTH peptide having intact amino-terminal ends is coupled to a solid phase, for example to Wang resin or polystyrol beads. The antibodies directed against the amino-terminal end PTH(1-3) are then bound, washed and eluted. The eluate is finally clarified by means of a second column, for which the hPTH peptide coupled to the solid phase has no intact amino-terminal epitope, for example as in the following peptide sequences SEQ No. 7 and SEQ No. 8.

SEQ No. 7
H$_2$N-Val$^2$-Ser$^3$-Glu$^4$-Ile$^5$-Gln$^6$-Leu$^7$-Met$^8$-His$^9$-Asn$^{10}$ - - - - carrier SEQ No. 8
H$_2$N-Ser$^3$-Glu$^4$-Ile$^5$-Gln$^6$-Leu$^7$-Met$^8$-His$^9$-Asn$^{10}$ - - - carrier In a per se known manner there can also be obtained in this way monoclonal antibodies against the amino-terminal epitope of PTH. Polyclonal antisera against the N-terminal hPTH epitope are however preferred. Naturally, the steps in the above-described purification can be exchanged or replaced and the PTH peptides used for the purification and clarification of the serum may be longer or shorter. It is necessary only that the amino-terminal epitope hPTH(1-3) be present intact in one case.

For obtaining the second antibody against the sequence of the receptor binding point of the PTH, intact hPTH(1-84) or biologically active hPTH(1-37) is synthesised, coupled to a carrier peptide and injected with complete Freund's adjuvant into an animal, for example, mouse, rat, rabbit or goat.

SEQ No. 9
Ser$^1$Val$^2$-Ser$^3$-Glu$^4$-Ile$^5$-Gln$^6$-Leu$^7$-Met$^8$-His$^9$-
Asn$^{10}$-Leu$^{11}$-Gly$^{12}$-Lys$^{13}$-His$^{14}$-Leu$^{15}$-Asn$^{16}$-Ser$^{17}$-
Met$^{18}$-Glu$^{19}$-Arg$^{20}$-Val$^{21}$-Glu$^{22}$-Trp$^{23}$-Leu$^{24}$-Arg$^{25}$-
Lys$^{26}$-Lys$^{27}$-Leu$^{28}$-Gln$^{29}$-Asp$^{30}$-Val$^{31}$-His$^{32}$-Asn$^{33}$-
Phe$^{34}$-Val$^{35}$-Ala$^{36}$-Leu$^{37}$

A coupling to a carrier peptide is not unavoidably necessary for generating an immune reaction, since the PTH sequences vary between human, cattle, pig and rat in particular in the region of the receptor binding point between positions 15 and 22 and are thus antigenic (see FIG. 2). In comparison with human PTH(1-37) fragments, bovine PTH differs for example at positions 1 (Ala), 7 (Phe) and 16 (Ser), rat PTH differs at positions 1 (Ala), 16 (Ala), 18 (Val) and 36 (Ser), porcine PTH differs at positions 16 (Ser) and 18 (Leu), and canine PTH differs at positions 7 (Ser) and 16 (Ser) (Heinrich G. et al (1984) J. Biol. Chem. 259:3320-3329; Kronenberg H. M. et al (1979) Proc. Natl. Acad. Sci. U.S.A. 76:4981-4985; Schmelzer H. -J., et al (1987) Nucleic Acids Res. 15:6740-6740; Rosol T. J. et al (1995) Gene 160:241-243). Coupling to a carrier recommends itself for the immunisation, since the mentioned peptides may not only be immunogenic but also biologically active.

The synthesis of hPTH(1-37) is effected as described in Example 2 of WO 91/06564. The above-mentioned peptides and their derivatives can also be produced through gene expression in a suitable procaryotic or eucaryotic host organism, and chromatographically purified. Along with the above-mentioned peptides, also the peptides hPTH(1-32), hPTH(1-33), hPTH(1-34), hPTH(1-38) and other biologically active hPTH fragments are suitable for obtaining antibodies against the receptor binding sequence of hPTH.

After several immunisation boosters with purified hPTH peptides or fragments, the immunoglobulin fraction is then isolated from the serum of the immunised animal and tested for its binding to the receptor point of hPTH. For this purpose the following heptapeptide hPTH(15-22)

SEQ Nr. 10
Leu$^{15}$-Asn$^{16}$-Ser$^{17}$-Met$^{18}$-Glu$^{19}$-Arg$^{20}$-Val$^{21}$-Glu$^{22}$ - - - carrier is synthesised on a macroscopic carrier such as polystyrol beads or polystyrol pins and antibodies which bind specifically the receptor binding structure of hPTH isolated by means of affinity chromatography. With the aid of the peptide-pin technique there can thus be captured also monoclonal antibodies against the receptor binding structure of PTH and clones, the antibodies of which recognise the receptor binding structure, can be separated. Of course, instead of the above-mentioned heptapeptide there can also be employed a hexapeptide or less long sequences of the receptor binding position.

With the antibodies against the N-terminal epitope of hPTH(1-3) and the receptor binding structure hPTH(15-22), antibodies are available which detect the functionally active structure.

In accordance with the invention, the immunoassay is effected on the active structure of hPTH under slightly denaturing conditions, so that in the unfolded peptide both epitopes are available for binding to the antibodies. This is effected by means of the otherwise unconventional addition of a detergent such as Tween™-20 or Triton™-X-100 in the binding buffer. The detergents are preferably added in a quantity of 0.01 to 1 weight percent, particularly preferably in a quantity from 0.1 to 0.3 weight percent, in the binding buffer.

Antagonistic hPTH fragments are characterised by a PTH receptor binding position and the lack of an intact amino-terminal epitope hPTH(1-3). The antagonistic activity of a sample is thus proportional to the number of PTH fragments which contain the receptor binding positions between positions 15 and 22 but which are not bound by antibodies against the amino-terminal epitope hPTH(1-3). The antagonistic activity can thus be determined from the difference between the number of molecules which are recognised by the antibody pair against the receptor binding position and the amino-terminus hPTH(1-3), and the number of fragments which are recognised by the antibody pair against the receptor binding structure (or a N-terminal epitope between amino acids 24 and 37) and an epitope in the region of the amino acids 4 and 14. The last-mentioned parameter is in practice equal to the number of hPTH fragments which are recognised by the antibody pair against the sections hPTH(9-18) and hPTH(24-34), but not by antibodies against the hPTH(1-3) epitope.

The antibodies against the region hPTH(4-14) arise in the purification of the antibodies against the hPTH(1-3) epitope. They are contained in the antibody fraction which binds to the amino-terminal peptide hPTH(2-10) with incomplete hPTH end epitope (see above). Such antibodies can be specifically produced, e.g. as in WO 96/10041 or in Tampe et al. (J. Immunoassay (1992), 13(1), pp. 1-13). So that the antibodies do not mutually disturb one another, it may here be advantageous to select two antibodies having binding points to hPTH (1-37) which lay somewhat further apart, for example as indicated above as an alternative. If the binding points lay too far apart or far toward the C-terminal of the receptor binding point between position 15 and 22 there is a risk that non-inhibiting hPTH fragments will be detected as antagonists.

The immunoassay in accordance with the invention of the biologically PTH activity can also be combined with existing PTH immunoassays. Thus, with some diagnoses there is to be indicated not only the biological activity of the hPTH, but also the quantity and distribution of hPTH molecules of a particular length. That means it can be of advantage to have a hPTH assay which along with the antibodies against the amino-terminal hPTH(1-3) also employs antibodies having mid-regional (53-68) or C-terminal (53-84) specificity. With such a PTH assay the effective PTH activity can then be placed in relationship to individual PTH molecules of particular length. By these means there can be explained in particular the causes of particular hyper- and hypo-parathyroidisms. In accordance with the invention the PTH activity assay includes also the additional determination of hPTH molecules having an intact carboxy terminus and antibodies against the mid-regional or C-terminal region of hPTH.

The method for determining the activity of PTH and its fragments in a sample can be realised as an EIA, ELISA, RIA, IRMA, LIA or ILMA, FIA or IFMA, as a manual test system or preferably in a version adapted for automatic systems, using liquid phase or solid phase techniques.

EXAMPLES

Example 1

Antibody Against the hPTH(1-3) Epitope

First, there is produced a threefold lysine branching on a Wang resin. For this purpose, to C-terminal alanine, bound to Wang resin, Fmoc-L-lysine(Fomc)-OH is bound in each case in three coupling cycles. The cleaving off of the Fmoc groups is then effected with 20% piperidine and 2% 1,8-diazabicyclo [5,4,0]undec-7-ene (DBU) in NN-dimethylformamide, NN-dimethylacetamide. The synthesis of the N-terminal hexapeptide hPTH (1-6) is then effected on the free amino groups in per se known manner by means of a solid phase synthesis and coupling of the C-terminal amino acids with the aid of dicyclohexylcarbodiimide as coupling means. The peptide $H_2N$-Ser$^1$-Val$^2$-Ser$^3$-Glu$^4$-Ile$^5$-Gln$^6$-(3×Lys)-Ala-carrier
(SEQ ID NO: 11)

is cleaved off from the carrier and unblocked at room temperature by means of 30 to 90 minutes treatment with trifluoroacetic acid, which contains 5% scavenger, water, ethanediol and phenol. The peptide is washed with trifluoroacetic acid, and precipitated with tert-butylmethylether from aqueous solution. The raw product is chromatographically purified through a C18-reverse phase column (10 µm, Buffer A: 0.01 N HCl in water; Buffer B: 20% isopropanol, 30% methanol, 50% water, 0.01 N HCl; gradient: 10-80% in 60 minutes precipitated).

1 mg purified peptide hPTH(1-6) is then coupled to 10 mg cattle serum albumin in aqueous solution at room temperature with the carboiimide method, and the coupled peptide precipitated out of the aqueous solution with isopropanol. The peptide was taken up in PBS and aliquoted.

For the first immunisation, 125 µg peptide carrier conjugate is dissolved in 250 µl PBS, emulsified with a double volume of complete Freund's adjuvant and the emulsion injected into a rabbit at various locations, in several units, subcutaneously. After 2 and 4 weeks there followed further booster injections with peptide and incomplete Freund's adjuvant.

After 6 weeks, 50 ml of blood was taken and antibodies against the amino-terminal hPTH(1-3) epitope obtained by means of sequential affinity chromatography through binding to protein-A, binding to the peptide hPTH(1-6) and clarification via a hPTH(2-10) peptide column. In the last-mentioned step there are precipitated after the further eluting also antibodies against hPTH(3-6), which can be employed for determining antagonistic PTH fragments.

Example 2

Antibodies Against the Receptor Binding Structure

The synthesis of hPTH(1-37) was effected as described in Example 2 of WO 91/06564. For the immunisation, 25 µg peptide hPTH(1-37), bound to Wang resin, in 50 µl PBS was injected intraperitoneally into a mouse. After 2 and 4 weeks there followed further boosters each with 50 µl peptide hPTH (1-37) on Wang resin. In per se known manner, monoclonal antibody clones were produced and the various pooled clones tested on hPTH(15-22)-heptapeptide, synthesised on polystyrol pins (see Tampe et al., J. Immunoassay (1992), 13(1), pp. 1-13). With four clones the binding epitopes with hPTH (1-10), hPTH(9-18), hPTH(16-24) and hPTH (24-37) were mapped and investigated for possible cross reactivity. FIG. 3 shows an analysis of the monoclonal antibodies against the receptor binding point of PTH and the cross-reactions with the further PTH fragments.

Example 3

Investigation of Cross-reactivity to Non-active Fragments

Synthetic hPTH(1-84) (Bachem AG) and various hPTH fragments with and without intact amino-terminal end epitopes were dissolved in similar quantities of serum and the resulting PTH activities, or the recovery of the biologically PTH fragments, determined in an immunoenzymometric assay (IEMA). As primary antibody there was used the monoclonal antibody mAK 13/C6315 against the receptor binding point and bound to the solid phase. The secondary antibody was polyclonal rabbit-anti-hPTH(1-3)-IgG. The colour reaction was effected with peroxidase conjugated goat-anti-rabbit-IgG and the ABTS system of Roche Diagnostics, Mannheim (ABTS=2,2'-azino-di-[3-ethylbenzthiazolin-sulfonate]. Extinction was measured at 405 nm.

FIGS. 4a and b show the cross-reaction with various hPTH fragments in two different trials. The results show that PTH fragments without the last two amino-terminal amino acids are not recognised in the test and all active PTH fragments form in substance an unitary group of characteristics. Differences result from differing degrees of purity of the preparations, weighing inaccuracies and the difficulties of exactly determining quantities in the case of peptides.

Example 4

Antibodies Against hPTH(4-14), hPTH(7 14) and hPTH(24-37)

There were produced two polyclonal antisera from goat and mouse and two monoclonal antibodies, which recognise the hPTH region between amino acids 7 and 14, as described in Tampe et al. (j. Immunoassay (1992) 13(1), pp 1-13). The antibodies against the hPTH(24-37) region and the hPTH(4-14) region were produced as described in WO 96/10041.

Example 5

Determination of the Effective PTH Activity in a Sample

In order to reduce the limit of detection, the concentration relationships were optimised and there was employed as detection system alkaline phosphatase together with a luminescence method. In the case of the employment of peroxidase and a luminescence method, pseudo-peroxidase present in blood plasma can disadvantageously increase the detection limit.

(i) Coating a Microtitration Plate with Monoclonal Antibodies Against the PTH Receptor Binding Structure There was placed into the depressions of a microtitration plate in each case 1.0 µg MAk 77/78 (subclone against receptor binding position hPTH (15-22)), dissolved in 250 µl 60 mM $NaHCO_3$, pH 9.6, and the plates incubated overnight at 4° C. The MAk solution in the depressions was removed and each depression washed five times with 200 µl washing buffer (PBS, pH 7.4 with 0.5% Tween-20). Then, 250 µl assay buffer was placed in each depression. For the assay buffer, 5 g casein was dissolved in 100 ml 0.1 N NaOH and topped up with PBS, pH 7.4, with 0.1 weight percent Triton™-X 100 to 1 L volume. The solution was boiled for one hour, the volume made up to 1 L with distilled water, the pH value set at 7.4 and 0.1 g thimerosal added for avoiding microbe growth. The depressions in the microtitration plate were incubated for one hour at room temperature with assay buffer, then the assay buffer was removed and each depression washed five times in each case with 200 µl washing buffer.

(ii) Sample Preparation

Venal blood was collected in EDTA vials (ca. 1.5 to 2 mg $K_2EDTA$ per millilitre blood), shaken, and after a clotting time of 10 to 15 minutes was centrifuged at 1800×G for 10 minutes. The plasma product was diluted 1:1 with assay buffer and stored at −20° C. until the test. If the samples contained more than 800 pMol/L PTH, the product was diluted 1:10 with assay buffer. Before use in the ELISA, the samples were centrifuged for short period at maximum revolutions.

(iii) Binding of Intact PTH(1-84) and PTH Fragments with Receptor Binding Structures In each case 100 µl diluted EDTA serum product in assay buffer was incubated for a half hour at room temperature in the pre-prepared depressions, whilst being shaken. Then the solutions were removed from the depressions and the depressions washed five times in each case with 200 µl washing buffer.

(iv) Determination of the Binding of Active PTH

In each case 100 µl affinity purified rabbit anti-PTH(1-3-epitope)-antiserum (1:10000 diluted in assay buffer with 3% (w/v) PEG 6000) was placed in the depressions and incubated for one hour in the dark, whilst being shaken, at room temperature. The solutions were then removed from the depressions and each depression washed five times in each case with 200 µl washing buffer. The quantitative determination was effected with 100 µl anti-rabbit-IgG, fc-specific, cross-absorbed and conjugated with alkaline phosphatase (1:20000 diluted in washing buffer). Incubation was effected for one hour at room temperature. Then, the antibody solution were removed and each depression washed five times in each case with 200 µl washing buffer. For the colour reaction there was placed in the depressions 100 µl Lumi-Phos™ Plus (ready-use solution with 4-methoxy-4-(3-phosphatephenyl)spirol[1,2-dioxetan-3,2'-adamantane]-disodium salt and associated enhancer (Lumigen, Mich., US) in 2-amino-2-methyl-1-propanol-buffer (pH 9.6)]. The measurement of the luminescence was then effected at 470 nm in a luminometer.

As standard there were employed solutions of PTH(1-84) in assay buffer having the following concentrations: 0, 0.1, 1, 10, 100 and 1000 pMol/L. The standard curve with alkaline phosphatase for the detection reaction shows that this system permits the determination of a few hundredths of pMol PTH per liter.

With the employment of peroxidase for the detection reaction, Lumigen™ PS-1 was employed as substrate. Briefly described, the wells of the microtitration plate were each washed five times with 250 µl washing buffer. Then, 50 µl standard or sample was pipetted into the well and finally 50 µl fresh 1:500 diluted second anti-hPTH(1-3) antibodies. Incubation took place overnight at 2 to 8° C. with gentle shaking, the content of the wells was removed and the well in each case washed five times with 250 µl washing buffer. For the detection reaction, 100 µl POD antibody conjugate (anti-rabbit-IgG fc-specific, cross-absorbed and conjugated with peroxidase; 1:20000 diluted in washing buffer) was added, and incubated for one hour at room temperature while being shaken, the solution removed and the wells washed five times with 250 µl washing buffer. The luminescence reaction was effected by means of the addition of 100 µl freshly mixed Lumigen™ PS substrate solution and incubation for five minutes at room temperature in the dark. There were then determined in a luminometer the relative light units (RLU). Due to the so-called pseudo-peroxidase present in the plasma the background was, however, higher, the sensitivity of the test was less.

(v) Determination of Antagonistic PTH Fragments

The antagonistic PTH activity potential was determined by coating a microtitration plate with monoclonal antibody against the region hPTH(7-14). There was placed into the wells of a microtitration plate in each case 1.0 µg MAk (clone against hPTH(7-14)), dissolved in 250 µl 60 mM $NaHCO_3$, pH 9.6, and the plate incubated overnight at 4° C. The MAk solution in the wells was removed and each well washed five times with 200 µl washing buffer (PBS, pH 7.4 with 0.05% Tween™-20). Then 250 µl assay buffer was placed in each well. The wells in the microtitration plate were incubated with assay buffer for one hour at room temperature, the assay buffer removed and each well washed five times in each case with 200 µl washing buffer. For the binding of antagonistic PTH fragments there was incubated, whilst shaking, in the well in each case 100 µl diluted EDTA serum product in assay buffer for a half hour at room temperature. The solution was removed from the wells and the wells washed five times in each case with 200 µl washing buffer. The bound antagonistic PTH fragments (7-37) were in each case marked with 100 µl affinity purified rabbit-anti-PTH(24-37) antiserum (1:10000 diluted in assay buffer with 3% (w/v) PEG 6000), as indicated above, and after washing with washing buffer quantitatively determined by means of the addition of 100 µl anti-rabbit-IgG fc-specific, cross-absorbed and conjugated with alkaline phosphatase (1:20000 diluted in washing buffer) and in analogous manner to the active PTH fragments, quantified by means of luminescence.

The molar difference determined in this method to the biologically active PTH fragments (having amino-terminal PTH(1-3) epitope) is then a measure for the PTH antagonistic potential in the sample. The antagonistic capacity of the PTH (4-37) fragments can, through a factor $k_{ant}$, be placed in relationship with the agonistic capacity of the biologically active PTH fragments hPTH(1-37) or hPTH(1-34), hPTH(1-38), hPTH(1-37+x) . . . hPTH(1-84).

As a rule it is sufficient if the agonistic and antagonistic proportions of the amino-terminal PTH fragments (i.e. amino-terminal of the amino acid 38) are placed in relationship 1:1. For some indications, however, it may be advantageous to place in relationship to one another the individual proportions of biologically active hPTH(1-84), hPTH(1-mid) [mid.=PTH fragments having mid-regional specificity 53-68], hPTH(1-Cterm) [Cterm=PTH fragments having C-terminal specificity 53-84] with the active hPTH(1-33~38) fragments and the inhibiting hPTH (4-37). The physiological hPTH activity can then in substance be determined as follows $$PTH - \text{Activity} = \frac{k_1[hPTH(1-32/38)] + k_x[hPTH(1-X/mid/cterm)] + K_2[hPTH(1-84)]}{k_3[hPTH(4-25 \text{ to } 84)]}$$

whereby k are factors for the agonistic and antagonistic activities of the various PTH fragments, and [hPTH(1-37)], [hPTH(1-84)], [hPTH(1-mid.)], [hPTH(1-Cterm)] and [hPTH(4-37)] are the concentrations of the various fragments in the sample. Thereby of course, the designation hPTH(1-33~38) includes fragments having 33 to 38 amino acids. As a rule, the constant $k_2$ for the fragments hPTH(1-mid.), hPTH(1-Cterm) and hPTH(1-84) will be approximately equal to $k_1$. For each individual PTH fragments an activity constant is to be determined if the activity constants $k_1$, $k_2$, $k_3$ . . . are to be different. The proportion of the fragments having mid-regional and C-terminal hPTH immune reactivity and an hPTH (1-3) epitope is then itself to be determined and this in analogous manner as for the agonistic and antagonistic fragments of the amino-terminal region.

As a rule, however, the following simplified equation will meet requirements.

$$PTH - \text{Activity} = \frac{k_1[hPTH(1-32 \text{ to } 38)] + k_2[hPTH(1-84)]}{k_3\{hPTH(4-25 \text{ to } 84)]}$$

whereby $k_1$, $k_2$ and $k_3$ can, as a first approximation, be made equal.

Example 6

Diagnosis of Primary Hyperparathyroidism

Case Study 1

Checking suspicion of hyperparathyroidism in a 57-year-old female patient having hypercalcaemia. A tumour hypercalcaemia was excluded by means of O-Sono, CT-Thorax, CT-Abdomen, MRT-Abdomen, gastroscopy and coloscopy. For the presence of a primary hyperparathyroidism there spoke the findings of hypophosphaturia, slightly increased cAMP excretion, an increased quotient of calcium clearance to creatinin clearance and further the clinical development with increasing calcium values, nephrocalcinosis with kidney deficiency, typical depressions, recurrent pancreatitis, and marginal osteopathy at the neck of the femur. Further, in the case of a tumour hypercalcaemia, a lesser PTH level would be expected. The relevant laboratory values from plasma were, however as follows:

| Parameter | Measurement Value | Normal Range |
|---|---|---|
| PTH intact | 1.5 | 12-6 pmol/ml |
| PTHrP | 1.8 | <2.5 |
| 25-hydroxy-vitamin-$D_3$ | 50 | 50 to 300 nmol/l |
| 1.25-vitamin-$D_3$ | 12 | 30 to 90 ng/l |

PTHrP: tumour-typical PTH

There was thus neither sarcoidosis or a vitamin-D originated hypercalcaemia. The values for 25-hydroxy-vitamin-$D_3$ and 1.25-vitamin-$D_3$ were too low for this. An attempted treatment with prednisone did not lead to a lowering of the calcium level. Further, in the case of a vitamin-D originated hypercalcaemia, a lower PTH level would be expected.

The determination of the biologically PTH activity with the aid of the assay in accordance with the invention, including also the activities of the fragments PTH(1-34), PTH(1-37), PTH(1-38) and amino-terminal parts of PTH(1-84), including intact PTH(1-84)—but not the PTH fragments PTH(3-37/38) and PTH(3-84)—showed an increased PTH activity in the serum of the patient (namely 37 pMol, 31 pMol, 22 pMol and 30 pMol bioactive PTH fragments per liter on four different days within one month), corresponding to 3 to 4 times of the normal PTH activity, so that the diagnosis of primary hyperparathyroidism was made plausible by the laboratory diagnosis. Due to the clearly increased PTH fragment 1 to 38 in the serum there could thus be assumed the secretion of an N-terminal fragment of PTH, whereas a kidney deficiency as a rule does not lead to an accumulation of N-terminal but of mid-regional and C-terminal fragments of PTH.

Case Study 2

For a 48-year-old dialysis patient having a disturbed calcium metabolism there was a suspicion of hyperparathyroidism. Sarcoidosis could be excluded on the basis of normal 1,25 hydroxy-vitamin-$D_3$ level. The patient was irregularly hypercalcaemic. For pathology, a bone biopsy was taken (bone cylinder 3 times each 1.2 cm). Microscopically, there could be seen a trabecular bone which at points was accompanied by a slightly endostalic fibrosis. On the bone surface there were increased resorption tracks, in part with active osteoclasts. The osteoblast activity was slightly increased. There was no strong osteoid formation. The bones were mostly of lamellar structure. In the marrow regions there was haematopoietic active bone marrow.

Apparently therefore there was an osteopathy of the type of a hyperparathyroidism. The osteopathy was active. The restructuring so far was slight. For a disturbance of mineralisation (osteoidosis, osteomalacoa) there was no indication. Likewise there was no indication for a plasmocytome. Despite this, the measurement values of intact PTH were not increased. The laboratory values were as follows.

| Time | Ca mmol/l | Phos mg/dl | Product <4.5 | PTH 12-72 pg/ml | AP | Bone U/l | 1.25-Vit.D ng/l | 25-vitD nmol/l |
|---|---|---|---|---|---|---|---|---|
| 04.12.00 | 2.79 | 2.80 | 2.52 | | | | | |
| 27.11.00 | 2.64 | 3.52 | 3.00 | | | | | |
| 20.11.00 | 2.39 | 2.47 | 1.90 | | | | | |
| 15.11.00 | 2.43 | 3.44 | 2.70 | | 247 | | | |
| 30.10.00 | 2.84 | 4.17 | 3.82 | | | | | |
| 23.10.00 | 2.88 | 4.76 | 4.43 | | | | | |
| 16.10.00 | 2.80 | 6.72 | 6.08 | 0 | 273 | 65 | | |
| 09.10.00 | 2.95 | 5.41 | 5.15 | | | | | |
| 06.10.00 | | | | 0 | | | 36.0 | 293.0 |
| 02.10.00 | 2.47 | 6.31 | 5.03 | | | | | |
| 19.09.00 | 2.96 | 6.01 | 5.74 | | | | | |
| 29.08.00 | 2.70 | 3.26 | 2.84 | | | | | |
| 15.08.00 | 3.14 | 5.87 | 5.95 | | | | | |
| 18.07.00 | | | | 1 | | 115 | | |
| 18.07.00 | 3.11 | 6.89 | 6.92 | | 320 | | | |
| 20.06.00 | 2.49 | 5.19 | 4.17 | | | | | |
| 16.05.00 | 2.23 | 3.44 | 2.48 | | | | | |
| 18.04.00 | 2.27 | 2.63 | 1.93 | | 241 | | | |
| 07.04.00 | | | | 5 | | 86 | | |
| 16.11.99 | 2.25 | 3.04 | 2.21 | | | | | |
| 19.10.99 | 2.38 | 3.23 | 2.48 | 7 | 234 | | | |
| 21.09.99 | 2.14 | | | | 224 | | | |
| 09.04.97 | 2.30 | | | | 174 | | | |
| 09.04.97 | 2.30 | | | | 174 | | | |

On the basis of these results a partial parathyroidectomy had been recommended. The immunoassay of the biologically effective PTH activity in accordance with the invention showed that also overall no increased PTH activity was present, so that the surgical treatment could be deferred.

The invention claimed is:

1. A method for determining the effective parathyroid hormone activity in a sample,
comprising the steps of:
(A) determining the agonist activity in a sample by reacting the sample with a first antibody which recognizes an epitope between amino acids 15 to 22 of the human parathyroid hormone (SEQ ID NO:16); reacting the sample with a second antibody which recognizes an epitope that is formed of the N-terminal amino acids 1-3 of the parathyroid hormone (SEQ ID NO:16) and contains the N-terminal amino acids; and determining the number of molecules which are recognized by the first and second antibodies; and
(B) determining the antagonist activity of a sample by reacting the sample with a third antibody which binds to the parathyroid hormone sequence (SEQ ID NO:16) between amino acids 4 to 14; reacting the sample with a fourth antibody which binds to the parathyroid hormone sequence (SEQ ID NO:16) between amino acids 15 to 37; and determining the number of molecules which are recognized by the third and fourth antibodies;
(C) placing the concentration of PTH molecules which are bound by the first and second antibodies, and the third and fourth antibodies, respectively, into a 1:1 relationship with one another to determine the physiologically effective parathyroid hormone activity; and
(D) calculating the physiologically effective parathyroid hormone activity using the following equation:

$$\text{PTH Activity} = \frac{\text{Concentration of Agonistic PTH Fragments (Step A)}}{\text{Concentration of Antagonistic PTH Fragments (Step B)}}.$$

2. The method according to claim 1, wherein the first antibody is bound to a solid phase and the second antibody carries a marker.

3. The method according to claim 1, wherein the binding of the first and second antibodies is effected in the presence of 0.05 to 0.1 weight percent of a mild detergent.

4. The method according to claim 2, wherein the binding of the first and second antibodies is effected in the presence of 0.05 to 0.1 weight percent of a mild detergent.

* * * * *

UNITED STATES PATENT AND TRADEMARK OFFICE
CERTIFICATE OF CORRECTION

PATENT NO. : 7,851,163 B2  
APPLICATION NO. : 10/168185  
DATED : December 14, 2010  
INVENTOR(S) : Franz Paul Armbruster et al.

Page 1 of 1

It is certified that error appears in the above-identified patent and that said Letters Patent is hereby corrected as shown below:

At column 20, claim number 1, line numbers 32-36, the equation should read:

$$\text{PTH Activity} = \frac{\text{Concentration of Agonistic PTH Fragments (Step A)}}{\text{Concentration of Antagonistic PTH Fragments (Step B)}}.$$

Signed and Sealed this  
Seventeenth Day of May, 2011

David J. Kappos  
*Director of the United States Patent and Trademark Office*